United States Patent
Claessens et al.

(10) Patent No.: US 12,201,734 B2
(45) Date of Patent: Jan. 21, 2025

(54) METHOD FOR STERILIZING HEART VALVES

(71) Applicant: Edwards Lifesciences Corporation, Irvine, CA (US)

(72) Inventors: Steven M. Claessens, Santa Rosa, CA (US); Rachel Ann Cooney, Costa Mesa, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 1042 days.

(21) Appl. No.: 17/054,505

(22) PCT Filed: Oct. 8, 2018

(86) PCT No.: PCT/US2018/054845
§ 371 (c)(1),
(2) Date: Nov. 10, 2020

(87) PCT Pub. No.: WO2019/074838
PCT Pub. Date: Apr. 18, 2019

(65) Prior Publication Data
US 2021/0187135 A1    Jun. 24, 2021

Related U.S. Application Data

(60) Provisional application No. 62/572,277, filed on Oct. 13, 2017.

(51) Int. Cl.
*A61L 2/00* (2006.01)
*A61F 2/02* (2006.01)
(Continued)

(52) U.S. Cl.
CPC .............. *A61L 2/007* (2013.01); *A61L 2/18* (2013.01); *A61L 27/3687* (2013.01); *A61L 2202/181* (2013.01); *A61L 2202/21* (2013.01)

(58) Field of Classification Search
CPC . A61L 2/007; A61L 2/18; A61L 27/27; A61L 2/0088; A61F 2/02; C12P 1/00
(Continued)

(56) References Cited

U.S. PATENT DOCUMENTS

| 3,143,742 A | 8/1964 | Cromie |
| 3,320,972 A | 5/1967 | High et al. |

(Continued)

FOREIGN PATENT DOCUMENTS

| EP | 0125393 A1 | 11/1984 |
| EP | 0143246 A2 | 6/1985 |

(Continued)

*Primary Examiner* — Monzer R Chorbaji
(74) *Attorney, Agent, or Firm* — Darren M. Franklin; Nathan Lee; Sheppard, Mullin, Richter & Hampton LLP (57) ABSTRACT

A method of preparing a sterilized heart valve, the method comprising: compressing a compressible frame of a heart valve from an expanded configuration to a crimped configuration; the heart valve comprising the frame and a plurality of leaflets coupled to the frame; wherein each of the plurality of leaflets comprises a dry, unfixed, decellularized, antigen-free biological tissue that has been treated with a solution comprising a polyol or polyhydric alcohol; packaging the heart valve within a sealed packaging system while the heart valve is in the crimped configuration; and sterilizing the heart valve packaged within the sealed packaging system with one or more cycles of electron beam radiation.

20 Claims, 9 Drawing Sheets

(51) Int. Cl.
*A61L 2/18* (2006.01)
*A61L 27/36* (2006.01)
*C08J 3/28* (2006.01)

(58) Field of Classification Search
USPC .................. 422/28; 623/11, 23.72; 424/426; 522/157
See application file for complete search history.

(56) References Cited

U.S. PATENT DOCUMENTS

| | | |
|---|---|---|
| 3,371,352 A | 3/1968 | Siposs et al. |
| 3,546,710 A | 12/1970 | Shumakov et al. |
| 3,574,865 A | 4/1971 | Hamaker |
| 3,755,823 A | 9/1973 | Hancock |
| 3,839,741 A | 10/1974 | Haller |
| 3,997,923 A | 12/1976 | Possis |
| 4,035,849 A | 7/1977 | Angell et al. |
| 4,079,468 A | 3/1978 | Liotta et al. |
| 4,084,268 A | 4/1978 | Ionescu et al. |
| 4,106,129 A | 8/1978 | Carpentier et al. |
| 4,172,295 A | 10/1979 | Batten |
| 4,217,665 A | 8/1980 | Bex et al. |
| 4,218,782 A | 8/1980 | Rygg |
| 4,259,753 A | 4/1981 | Liotta et al. |
| RE30,912 E | 4/1982 | Hancock |
| 4,340,091 A | 7/1982 | Skelton et al. |
| 4,343,048 A | 8/1982 | Ross et al. |
| 4,364,126 A | 12/1982 | Rosen et al. |
| 4,388,735 A | 6/1983 | Ionescu et al. |
| 4,441,216 A | 4/1984 | Tonescu et al. |
| 4,451,936 A | 6/1984 | Carpentier et al. |
| 4,470,157 A | 9/1984 | Love |
| 4,490,859 A | 1/1985 | Black et al. |
| 4,501,030 A | 2/1985 | Lane |
| 4,506,394 A | 3/1985 | Bedard |
| 4,535,483 A | 8/1985 | Klawitter et al. |
| 4,566,465 A | 1/1986 | Arhan et al. |
| 4,605,407 A | 8/1986 | Black et al. |
| 4,626,255 A | 12/1986 | Reichart et al. |
| 4,629,459 A | 12/1986 | Ionescu et al. |
| 4,680,031 A | 7/1987 | Alonso |
| 4,687,483 A | 8/1987 | Fisher et al. |
| 4,705,516 A | 11/1987 | Barone et al. |
| 4,725,274 A | 2/1988 | Lane et al. |
| 4,731,074 A | 3/1988 | Rousseau et al. |
| 4,778,461 A | 10/1988 | Pietsch et al. |
| 4,790,843 A | 12/1988 | Carpentier et al. |
| 4,851,000 A | 7/1989 | Gupta |
| 4,888,009 A | 12/1989 | Lederman et al. |
| 4,914,097 A | 4/1990 | Oda et al. |
| 4,960,424 A | 10/1990 | Grooters |
| 4,993,428 A | 2/1991 | Arms |
| 5,010,892 A | 4/1991 | Colvin et al. |
| 5,032,128 A | 7/1991 | Alonso |
| 5,037,434 A | 8/1991 | Lane |
| 5,147,391 A | 9/1992 | Lane |
| 5,163,955 A | 11/1992 | Love et al. |
| 5,258,023 A | 11/1993 | Reger |
| 5,316,016 A | 5/1994 | Adams et al. |
| 5,326,370 A | 7/1994 | Love et al. |
| 5,326,371 A | 7/1994 | Love et al. |
| 5,332,402 A | 7/1994 | Teitelbaum |
| 5,360,014 A | 11/1994 | Sauter et al. |
| 5,360,444 A | 11/1994 | Kusuhara |
| 5,376,112 A | 12/1994 | Duran |
| 5,396,887 A | 3/1995 | Imran |
| 5,397,351 A | 3/1995 | Pavcnik et al. |
| 5,423,887 A | 6/1995 | Love et al. |
| 5,425,741 A | 6/1995 | Lemp et al. |
| 5,431,676 A | 7/1995 | Dubrul et al. |
| 5,449,384 A | 9/1995 | Johnson |
| 5,449,385 A | 9/1995 | Religa et al. |
| 5,469,868 A | 11/1995 | Reger |
| 5,487,760 A | 1/1996 | Villafana |
| 5,488,789 A | 2/1996 | Religa et al. |
| 5,489,296 A | 2/1996 | Love et al. |
| 5,489,297 A | 2/1996 | Duran |
| 5,489,298 A | 2/1996 | Love et al. |
| 5,500,016 A | 3/1996 | Fisher |
| 5,507,810 A * | 4/1996 | Prewett ............... A61L 27/3691 623/23.72 |
| 5,533,515 A | 7/1996 | Coller et al. |
| 5,549,665 A | 8/1996 | Vesely et al. |
| 5,562,729 A | 10/1996 | Purdy et al. |
| 5,571,215 A | 11/1996 | Sterman et al. |
| 5,573,007 A | 11/1996 | Bobo, Sr. |
| 5,578,076 A | 11/1996 | Krueger et al. |
| 5,584,803 A | 12/1996 | Stevens et al. |
| 5,618,307 A | 4/1997 | Donlon et al. |
| 5,626,607 A | 5/1997 | Malecki et al. |
| 5,628,789 A | 5/1997 | Vanney et al. |
| 5,693,090 A | 12/1997 | Unsworth et al. |
| 5,695,503 A | 12/1997 | Krueger et al. |
| 5,713,952 A | 2/1998 | Vanney et al. |
| 5,716,370 A | 2/1998 | Williamson, IV et al. |
| 5,728,064 A | 3/1998 | Burns et al. |
| 5,728,151 A | 3/1998 | Garrison et al. |
| 5,735,894 A | 4/1998 | Krueger et al. |
| 5,752,522 A | 5/1998 | Murphy |
| 5,755,782 A | 5/1998 | Love et al. |
| 5,766,240 A | 6/1998 | Johnson |
| 5,800,527 A | 9/1998 | Jansen et al. |
| 5,814,097 A | 9/1998 | Sterman et al. |
| 5,814,098 A | 9/1998 | Hinnenkamp et al. |
| 5,824,064 A | 10/1998 | Taheri |
| 5,824,068 A | 10/1998 | Bugge |
| 5,840,081 A | 11/1998 | Andersen et al. |
| 5,848,969 A | 12/1998 | Panescu et al. |
| 5,855,563 A | 1/1999 | Kaplan et al. |
| 5,855,601 A | 1/1999 | Bessler et al. |
| 5,855,801 A | 1/1999 | Lin et al. |
| 5,891,160 A | 4/1999 | Williamson, IV et al. |
| 5,895,420 A | 4/1999 | Mirsch, II et al. |
| 5,902,308 A | 5/1999 | Murphy |
| 5,908,450 A | 6/1999 | Gross et al. |
| 5,919,147 A | 7/1999 | Jain |
| 5,921,934 A | 7/1999 | Teo |
| 5,921,935 A | 7/1999 | Hickey |
| 5,924,984 A | 7/1999 | Rao |
| 5,957,949 A | 9/1999 | Leonhardt et al. |
| 5,972,004 A | 10/1999 | Williamson, IV et al. |
| 5,984,959 A | 11/1999 | Robertson et al. |
| 5,984,973 A | 11/1999 | Girard et al. |
| 6,010,531 A | 1/2000 | Donlon et al. |
| 6,042,554 A | 3/2000 | Rosenman et al. |
| 6,042,607 A | 3/2000 | Williamson, IV et al. |
| 6,066,160 A | 5/2000 | Colvin et al. |
| 6,074,418 A | 6/2000 | Buchanan et al. |
| 6,081,737 A | 6/2000 | Shah |
| 6,083,179 A | 7/2000 | Oredsson |
| 6,099,475 A | 8/2000 | Seward et al. |
| 6,106,550 A | 8/2000 | Magovern et al. |
| 6,110,200 A | 8/2000 | Hinnenkamp |
| 6,117,091 A | 9/2000 | Young et al. |
| 6,126,007 A | 10/2000 | Kari et al. |
| 6,162,233 A | 12/2000 | Williamson, IV et al. |
| 6,168,614 B1 | 1/2001 | Andersen et al. |
| 6,176,877 B1 | 1/2001 | Buchanan et al. |
| 6,197,054 B1 | 3/2001 | Hamblin, Jr. et al. |
| 6,217,611 B1 | 4/2001 | Klostermeyer |
| 6,231,561 B1 | 5/2001 | Frazier et al. |
| 6,241,765 B1 | 6/2001 | Griffin et al. |
| 6,245,102 B1 | 6/2001 | Jayaraman |
| 6,264,611 B1 | 7/2001 | Ishikawa et al. |
| 6,283,127 B1 | 9/2001 | Sterman et al. |
| 6,287,339 B1 | 9/2001 | Vazquez et al. |
| 6,290,674 B1 | 9/2001 | Roue et al. |
| 6,312,447 B1 | 11/2001 | Grimes |
| 6,312,465 B1 | 11/2001 | Griffin et al. |
| 6,328,727 B1 | 12/2001 | Frazier et al. |
| 6,350,282 B1 | 2/2002 | Eberhardt |
| 6,371,983 B1 | 4/2002 | Lane |
| 6,375,620 B1 | 4/2002 | Oser et al. |

(56) References Cited

U.S. PATENT DOCUMENTS

| | | |
|---|---|---|
| 6,402,780 B2 | 6/2002 | Williamson, IV et al. |
| 6,409,674 B1 | 6/2002 | Brockway et al. |
| 6,425,916 B1 | 7/2002 | Garrison et al. |
| 6,440,164 B1 | 8/2002 | DiMatteo et al. |
| 6,442,413 B1 | 8/2002 | Silver |
| 6,454,799 B1 | 9/2002 | Schreck |
| 6,458,153 B1 | 10/2002 | Bailey et al. |
| 6,468,305 B1 | 10/2002 | Otte |
| 6,491,624 B1 | 12/2002 | Lotfi |
| 6,582,462 B1 | 6/2003 | Andersen et al. |
| 6,585,766 B1 | 7/2003 | Huynh et al. |
| 6,645,143 B2 | 11/2003 | VanTassel et al. |
| 6,652,464 B2 | 11/2003 | Schwartz et al. |
| 6,652,578 B2 | 11/2003 | Bailey et al. |
| 6,675,049 B2 | 1/2004 | Thompson et al. |
| 6,682,559 B2 | 1/2004 | Myers et al. |
| 6,685,739 B2 | 2/2004 | DiMatteo et al. |
| 6,730,118 B2 | 5/2004 | Spenser et al. |
| 6,733,525 B2 | 5/2004 | Yang et al. |
| 6,741,885 B1 | 5/2004 | Park et al. |
| 6,764,508 B1 | 7/2004 | Roehe et al. |
| 6,767,362 B2 | 7/2004 | Schreck |
| 6,773,457 B2 | 8/2004 | Ivancev et al. |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,795,732 B2 | 9/2004 | Stadler et al. |
| 6,805,711 B2 | 10/2004 | Quijano et al. |
| 6,893,459 B1 | 5/2005 | Macoviak |
| 6,893,460 B2 | 5/2005 | Spenser et al. |
| 6,895,265 B2 | 5/2005 | Silver |
| 6,908,481 B2 | 6/2005 | Cribier |
| 6,939,365 B1 | 9/2005 | Fogarty et al. |
| 7,011,681 B2 | 3/2006 | Vesely |
| 7,025,780 B2 | 4/2006 | Gabbay |
| 7,033,322 B2 | 4/2006 | Silver |
| 7,052,466 B2 | 5/2006 | Scheiner et al. |
| 7,070,616 B2 | 7/2006 | Majercak et al. |
| 7,082,330 B2 | 7/2006 | Stadler et al. |
| 7,097,659 B2 | 8/2006 | Woolfson et al. |
| 7,101,396 B2 | 9/2006 | Artof et al. |
| 7,147,663 B1 | 12/2006 | Berg et al. |
| 7,153,324 B2 | 12/2006 | Case et al. |
| 7,195,641 B2 | 3/2007 | Palmaz et al. |
| 7,201,771 B2 | 4/2007 | Lane |
| 7,201,772 B2 | 4/2007 | Schwammenthal et al. |
| 7,238,200 B2 | 7/2007 | Lee et al. |
| 7,252,682 B2 | 8/2007 | Seguin |
| 7,261,732 B2 | 8/2007 | Justino |
| RE40,377 E | 6/2008 | Williamson, IV et al. |
| 7,416,530 B2 | 8/2008 | Turner et al. |
| 7,422,603 B2 | 9/2008 | Lane |
| 7,513,909 B2 | 4/2009 | Lane et al. |
| 7,556,647 B2 | 7/2009 | Drews et al. |
| 7,569,072 B2 | 8/2009 | Berg et al. |
| 7,621,878 B2 | 11/2009 | Ericson et al. |
| 7,916,013 B2 | 3/2011 | Stevenson |
| 7,998,151 B2 | 8/2011 | St. Goar et al. |
| 8,066,650 B2 | 11/2011 | Lee et al. |
| 8,248,232 B2 | 8/2012 | Stevenson et al. |
| 8,253,555 B2 | 8/2012 | Stevenson et al. |
| 8,340,750 B2 | 12/2012 | Prakash et al. |
| 8,401,659 B2 | 3/2013 | Von Arx et al. |
| 8,529,474 B2 | 9/2013 | Gupta et al. |
| 8,622,936 B2 | 1/2014 | Schenberger et al. |
| 9,101,264 B2 | 8/2015 | Acquista |
| 9,101,281 B2 | 8/2015 | Reinert et al. |
| 9,693,862 B2 | 7/2017 | Campbell et al. |
| 2001/0039435 A1 | 11/2001 | Roue et al. |
| 2001/0039436 A1 | 11/2001 | Frazier et al. |
| 2001/0041914 A1 | 11/2001 | Frazier et al. |
| 2001/0041915 A1 | 11/2001 | Roue et al. |
| 2001/0049492 A1 | 12/2001 | Frazier et al. |
| 2002/0020074 A1 | 2/2002 | Love et al. |
| 2002/0026238 A1 | 2/2002 | Lane et al. |
| 2002/0032481 A1 | 3/2002 | Gabbay |
| 2002/0058995 A1 | 5/2002 | Stevens |
| 2002/0123802 A1 | 9/2002 | Snyders |
| 2002/0138138 A1 | 9/2002 | Yang |
| 2002/0151970 A1 | 10/2002 | Garrison et al. |
| 2002/0188348 A1 | 12/2002 | DiMatteo et al. |
| 2002/0198594 A1 | 12/2002 | Schreck |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0036795 A1 | 2/2003 | Andersen et al. |
| 2003/0040792 A1 | 2/2003 | Gabbay |
| 2003/0055495 A1 | 3/2003 | Pease et al. |
| 2003/0105519 A1 | 6/2003 | Fasol et al. |
| 2003/0109924 A1 | 6/2003 | Cribier |
| 2003/0114913 A1 | 6/2003 | Spenser et al. |
| 2003/0130729 A1 | 7/2003 | Paniagua et al. |
| 2003/0149478 A1 | 8/2003 | Figulla et al. |
| 2003/0167089 A1 | 9/2003 | Lane |
| 2003/0236568 A1 | 12/2003 | Hojeibane et al. |
| 2004/0010296 A1 | 1/2004 | Swanson et al. |
| 2004/0019374 A1 | 1/2004 | Hojeibane et al. |
| 2004/0027306 A1 | 2/2004 | Amundson et al. |
| 2004/0034411 A1 | 2/2004 | Quijano et al. |
| 2004/0044406 A1 | 3/2004 | Woolfson et al. |
| 2004/0106976 A1 | 6/2004 | Bailey et al. |
| 2004/0122514 A1 | 6/2004 | Fogarty et al. |
| 2004/0122516 A1 | 6/2004 | Fogarty et al. |
| 2004/0167573 A1 | 8/2004 | Williamson et al. |
| 2004/0186563 A1 | 9/2004 | Lobbi |
| 2004/0186565 A1 | 9/2004 | Schreck |
| 2004/0193261 A1 | 9/2004 | Berreklouw |
| 2004/0206363 A1 | 10/2004 | McCarthy et al. |
| 2004/0210304 A1 | 10/2004 | Seguin et al. |
| 2004/0210307 A1 | 10/2004 | Khairkhahan |
| 2004/0225355 A1 | 11/2004 | Stevens |
| 2004/0236411 A1 | 11/2004 | Sarac et al. |
| 2004/0260389 A1 | 12/2004 | Case et al. |
| 2004/0260390 A1 | 12/2004 | Sarac et al. |
| 2005/0010285 A1 | 1/2005 | Lambrecht et al. |
| 2005/0027348 A1 | 2/2005 | Case et al. |
| 2005/0033398 A1 | 2/2005 | Seguin |
| 2005/0043760 A1 | 2/2005 | Fogarty et al. |
| 2005/0043790 A1 | 2/2005 | Seguin |
| 2005/0060029 A1 | 3/2005 | Le et al. |
| 2005/0065594 A1 | 3/2005 | DiMatteo et al. |
| 2005/0065614 A1 | 3/2005 | Stinson |
| 2005/0075584 A1 | 4/2005 | Cali |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0080454 A1 | 4/2005 | Drews et al. |
| 2005/0096738 A1 | 5/2005 | Cali et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137690 A1 | 6/2005 | Salahieh et al. |
| 2005/0137692 A1 | 6/2005 | Haug et al. |
| 2005/0137695 A1 | 6/2005 | Salahieh et al. |
| 2005/0159811 A1 | 7/2005 | Lane |
| 2005/0165479 A1 | 7/2005 | Drews et al. |
| 2005/0182486 A1 | 8/2005 | Gabbay |
| 2005/0192665 A1 | 9/2005 | Spenser et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0216079 A1 | 9/2005 | MaCoviak |
| 2005/0222674 A1 | 10/2005 | Paine |
| 2005/0234546 A1 | 10/2005 | Nugent et al. |
| 2005/0240263 A1 | 10/2005 | Fogarty et al. |
| 2005/0251252 A1 | 11/2005 | Stobie |
| 2005/0261765 A1 | 11/2005 | Liddicoat |
| 2005/0283231 A1 | 12/2005 | Haug et al. |
| 2006/0025857 A1 | 2/2006 | Bergheim et al. |
| 2006/0052867 A1 | 3/2006 | Revuelta et al. |

(56) References Cited

U.S. PATENT DOCUMENTS

| | | |
|---|---|---|
| 2006/0058871 A1 | 3/2006 | Zakay et al. |
| 2006/0058872 A1 | 3/2006 | Salahieh et al. |
| 2006/0074484 A1 | 4/2006 | Huber |
| 2006/0085060 A1 | 4/2006 | Campbell |
| 2006/0095125 A1 | 5/2006 | Chinn et al. |
| 2006/0122634 A1 | 6/2006 | Ino et al. |
| 2006/0149360 A1 | 7/2006 | Schwammenthal et al. |
| 2006/0154230 A1 | 7/2006 | Cunanan et al. |
| 2006/0167543 A1 | 7/2006 | Bailey et al. |
| 2006/0195184 A1 | 8/2006 | Lane et al. |
| 2006/0195185 A1 | 8/2006 | Lane et al. |
| 2006/0195186 A1 | 8/2006 | Drews et al. |
| 2006/0207031 A1 | 9/2006 | Cunanan et al. |
| 2006/0241745 A1 | 10/2006 | Solem |
| 2006/0259136 A1 | 11/2006 | Nguyen et al. |
| 2006/0271172 A1 | 11/2006 | Tehrani |
| 2006/0271175 A1 | 11/2006 | Woolfson et al. |
| 2006/0287717 A1 | 12/2006 | Rowe et al. |
| 2006/0287719 A1 | 12/2006 | Rowe et al. |
| 2007/0005129 A1 | 1/2007 | Damm et al. |
| 2007/0010876 A1 | 1/2007 | Salahieh et al. |
| 2007/0016285 A1 | 1/2007 | Lane et al. |
| 2007/0016286 A1 | 1/2007 | Herrmann et al. |
| 2007/0016288 A1 | 1/2007 | Gurskis et al. |
| 2007/0043435 A1 | 2/2007 | Seguin et al. |
| 2007/0078509 A1 | 4/2007 | Lotfy |
| 2007/0078510 A1 | 4/2007 | Ryan |
| 2007/0100440 A1 | 5/2007 | Figulla et al. |
| 2007/0129794 A1 | 6/2007 | Realyvasquez |
| 2007/0142906 A1 | 6/2007 | Figulla et al. |
| 2007/0142907 A1 | 6/2007 | Moaddeb et al. |
| 2007/0150053 A1 | 6/2007 | Gurskis et al. |
| 2007/0156233 A1 | 7/2007 | Kapadia et al. |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0179604 A1 | 8/2007 | Lane |
| 2007/0185565 A1 | 8/2007 | Schwammenthal et al. |
| 2007/0198097 A1 | 8/2007 | Zegd |
| 2007/0203575 A1 | 8/2007 | Forster et al. |
| 2007/0203576 A1 | 8/2007 | Lee et al. |
| 2007/0213813 A1 | 9/2007 | Von Segesser et al. |
| 2007/0225801 A1 | 9/2007 | Drews et al. |
| 2007/0233237 A1 | 10/2007 | Krivoruchko |
| 2007/0239266 A1 | 10/2007 | Birdsall |
| 2007/0239269 A1 | 10/2007 | Dolan et al. |
| 2007/0239273 A1 | 10/2007 | Allen |
| 2007/0255398 A1 | 11/2007 | Yang et al. |
| 2007/0260305 A1 | 11/2007 | Drews et al. |
| 2007/0265369 A1* | 11/2007 | Muratoglu ............. B29C 35/08 264/479 |
| 2007/0265701 A1 | 11/2007 | Gurskis et al. |
| 2007/0270944 A1 | 11/2007 | Bergheim et al. |
| 2007/0282436 A1 | 12/2007 | Pinchuk |
| 2007/0288089 A1 | 12/2007 | Gurskis et al. |
| 2008/0033543 A1 | 2/2008 | Gurskis et al. |
| 2008/0046040 A1 | 2/2008 | Denker et al. |
| 2008/0119875 A1 | 5/2008 | Ino et al. |
| 2008/0154356 A1 | 6/2008 | Obermiller et al. |
| 2008/0319543 A1 | 12/2008 | Lane |
| 2009/0036903 A1 | 2/2009 | Ino et al. |
| 2009/0192591 A1 | 7/2009 | Ryan et al. |
| 2009/0192599 A1 | 7/2009 | Lane et al. |
| 2010/0049313 A1 | 2/2010 | Alon et al. |
| 2010/0145438 A1 | 6/2010 | Barone |
| 2010/0256723 A1 | 10/2010 | Murray |
| 2012/0059487 A1* | 3/2012 | Cunanan ............. A61L 27/3695 623/23.72 |
| 2012/0123284 A1 | 5/2012 | Kheradvar |
| 2012/0296382 A1 | 11/2012 | Shuros et al. |
| 2013/0144379 A1 | 6/2013 | Najafi et al. |
| 2014/0128964 A1 | 5/2014 | Delaloye |
| 2014/0188221 A1 | 7/2014 | Chung et al. |
| 2014/0364707 A1 | 12/2014 | Kintz et al. |
| 2015/0045635 A1 | 2/2015 | Tankiewicz et al. |
| 2016/0045316 A1 | 2/2016 | Braido et al. |
| 2016/0184096 A1 | 6/2016 | Maimon et al. |
| 2017/0056149 A1* | 3/2017 | Rajpara ................. A61F 2/0095 |
| 2019/0321170 A1 | 10/2019 | Green et al. |

FOREIGN PATENT DOCUMENTS

| | | | |
|---|---|---|---|
| SU | 1116573 A1 | 7/1985 | |
| SU | 1697790 A1 | 12/1991 | |
| WO | 9213502 A1 | 8/1992 | |
| WO | WO-9523616 A1 * | 9/1995 | ............... A61F 2/06 |
| WO | 9742871 A1 | 11/1997 | |
| WO | 0170577 A1 | 9/2001 | |
| WO | WO-2012094435 A2 * | 7/2012 | ............ A61F 2/2412 |
| WO | 2017040684 A1 | 3/2017 | |
| WO | 2018204455 A1 | 11/2018 | |

\* cited by examiner

METHOD FOR STERILIZING HEART VALVES

This application is a National Stage of International Patent Application No. PCT/US2018/054845, filed Oct. 8, 2018, which claims the benefit of U.S. Patent Application No. 62/572,277, filed Oct. 13, 2017, the entire contents all of which are incorporated into this application by reference for all purposes.

This disclosure relates generally to heart valves and, more particularly, to a method of preparing a sterilized transcatheter heart valve using electron beam sterilization.

Transcatheter heart valves are packaged and sterilized at a manufacturing site before they are shipped to an operation site. Currently, a heart valve is crimped at the operation site, whereupon a doctor implants the device. This process of crimping the heart valve at the operation site is inefficient and costly, and it creates opportunities for error.

It should be appreciated that there is a need for a method of preparing a transcatheter heart valve that can be crimped, packaged, and sterilized at the manufacturer's site. The present invention fulfills this need and provides further related advantages.

Some embodiments disclosed herein provide methods for preparing a sterilized heart valve. In one embodiment, the method can comprise compressing a compressible frame of a heart valve from an expanded configuration to a crimped configuration, packaging the heart valve within a sealed packaging system while the heart valve is in the crimped configuration, and sterilizing the heart valve packaged within the sealed packaging system with one or more cycles of electron beam radiation. The heart valve can comprise the frame and a plurality of leaflets coupled to the frame. Each of the plurality of leaflets can comprise an unfixed, decellularized, antigen-free biological tissue that has been treated with a solution comprising a polyol or polyhydric alcohol.

In one embodiment, each of the one or more cycles of electron beam radiation can comprise a dose of about 15-40 kGy. In another embodiment, each of the one or more cycles of electron beam radiation can comprise a dose of about 15-20 kGy.

In one embodiment, the heart valve packaged within the sealed packaging system can be sterilized with two or more cycles of electron beam radiation. In an additional embodiment, the heart valve packaged within the sealed packaging system can be sterilized with three cycles of electron beam radiation.

In one embodiment, the polyol or polyhydric alcohol can comprise glycerol.

In one embodiment, the method can further comprise coupling the heart valve to a delivery system.

In one embodiment, the biological tissue is pericardial tissue. In another embodiment, the biological tissue is pericardial tissue selected from the group consisting of porcine pericardial tissue and bovine pericardial tissue.

In one embodiment, the method can further comprise loading the heart valve within a sheath associated with the delivery system. In another embodiment, the loading step can be performed by causing the sheath to move axially over the heart valve.

In one embodiment, the frame can be at least partially crimped in the crimped configuration. In another embodiment, the frame can be fully crimped in the crimped configuration. The heart valve can have a first diameter in the expanded configuration and a second diameter in the crimped configuration. In a further embodiment, the second diameter can be smaller than the first diameter. In an additional embodiment, the second diameter can be less than about 50% of the first diameter. In yet another embodiment, the second diameter can be about 10% of the first diameter.

In one embodiment, the method can further comprise refrigerating the heart valve and the packaging system before the sterilizing step. In another embodiment, the heart valve does not comprise fluorinated materials. In an additional embodiment, the packaging system does not contain a liquid storage solution.

Each feature, concept, or step is independent, but can be combined with any other feature, concept, or step disclosed in this application.

In one embodiment, a method of preparing a sterilized heart valve can comprise treating a plurality of leaflets with a solution comprising a polyol or polyhydric alcohol. Each of the plurality of leaflets can comprise a dry, unfixed, decellularized, antigen-free biological tissue. The method can further comprise forming a heart valve, wherein the forming step can comprise coupling each of the plurality of leaflets to a compressible frame. In one embodiment, the method can further comprise compressing the frame from an expanded configuration to a crimped configuration. In another embodiment, the method can further comprise packaging the heart valve within a sealed packaging system while the heart valve is in the crimped configuration. In a further embodiment, the method can further comprise sterilizing the heart valve packaged within the sealed packaging system with one or more cycles of electron beam radiation.

In one embodiment, each of the one or more cycles of electron beam radiation can comprise a dose of about 15-40 kGy. In another embodiment, each of the one or more cycles of radiation can comprise a dose of about 15-20 kGy.

In one embodiment, the heart valve packaged within the sealed packaging system can be sterilized with two or more cycles of electron beam radiation. In another embodiment, the heart valve packaged within the sealed packaging system can be sterilized with three cycles of electron beam radiation.

In one embodiment, the polyol or polyhydric alcohol comprises glycerol.

In one embodiment, the method can further comprise coupling the heart valve to a delivery system.

In one embodiment, the biological tissue is pericardial tissue. In another embodiment, the biological tissue is pericardial tissue selected from the group consisting of porcine pericardial tissue and bovine pericardial tissue.

In one embodiment, the method can further comprise loading the heart valve within a sheath associated with the delivery system. In another embodiment, the loading step can be performed by causing the sheath to move axially over the heart valve.

In one embodiment, the frame can be at least partially crimped in the crimped configuration. In another embodiment, the frame can be fully crimped in the crimped configuration. The heart valve can have a first diameter in the expanded configuration and a second diameter in the crimped configuration. In a further embodiment, the second diameter can be smaller than the first diameter. In an additional embodiment, the second diameter can be less than about 50% of the first diameter. In yet another embodiment, the second diameter can be about 10% of the first diameter.

In one embodiment, the method can further comprise refrigerating the heart valve and the packaging system before the sterilizing step. In another embodiment, the heart valve does not comprise fluorinated materials. In an additional embodiment, the packaging system does not contain a liquid storage solution.

Each feature, concept, or step is independent, but can be combined with any other feature, concept, or step disclosed in this application.

In one embodiment, a method of preparing a sterilized heart valve can comprise coupling a heart valve to a delivery system. The heart valve can comprise a compressible frame and a plurality of leaflets coupled to the frame. In another embodiment, each of the plurality of leaflets can comprise a dry, unfixed, decellularized, antigen-free biological tissue. The method can further comprise compressing the frame of the heart valve from an expanded configuration to a crimped configuration. In one embodiment, the method can further comprise packaging the heart valve within a sealed packaging system while the heart valve is in the crimped configuration. In another embodiment, the method can further comprise sterilizing the heart valve packaged within the sealed packaging system with one or more cycles of electron beam radiation.

In one embodiment, each of the one or more cycles of electron beam radiation can comprise a dose of about 15-40 kGy. In another embodiment, each of the one or more cycles of radiation can comprise a dose of about 15-20 kGy.

In one embodiment, the heart valve packaged within the sealed packaging system can be sterilized with two or more cycles of electron beam radiation. In another embodiment, the heart valve packaged within the sealed packaging system can be sterilized with three cycles of electron beam radiation.

In one embodiment, the biological tissue is pericardial tissue. In another embodiment, the biological tissue is pericardial tissue selected from the group consisting of porcine pericardial tissue and bovine pericardial tissue.

In one embodiment, the method can further comprise loading the heart valve within a sheath associated with the delivery system. In another embodiment, the loading step can be performed by causing the sheath to move axially over the heart valve.

In one embodiment, the frame can be at least partially crimped in the crimped configuration. In another embodiment, the frame can be fully crimped in the crimped configuration. The heart valve can have a first diameter in the expanded configuration and a second diameter in the crimped configuration. In a further embodiment, the second diameter can be smaller than the first diameter. In an additional embodiment, the second diameter can be less than about 50% of the first diameter. In yet another embodiment, the second diameter can be about 10% of the first diameter.

In one embodiment, the method can further comprise refrigerating the heart valve and the packaging system before the sterilizing step. In another embodiment, the heart valve does not comprise fluorinated materials. In a further embodiment, the packaging system does not contain a liquid storage solution.

Each feature, concept, or step is independent, but can be combined with any other feature, concept, or step disclosed in this application.

Other features and advantages of the invention should become apparent from the following description of the preferred embodiments, taken in conjunction with the accompanying drawings, which illustrate, by way of example, the principles of the invention.

Figure 1:
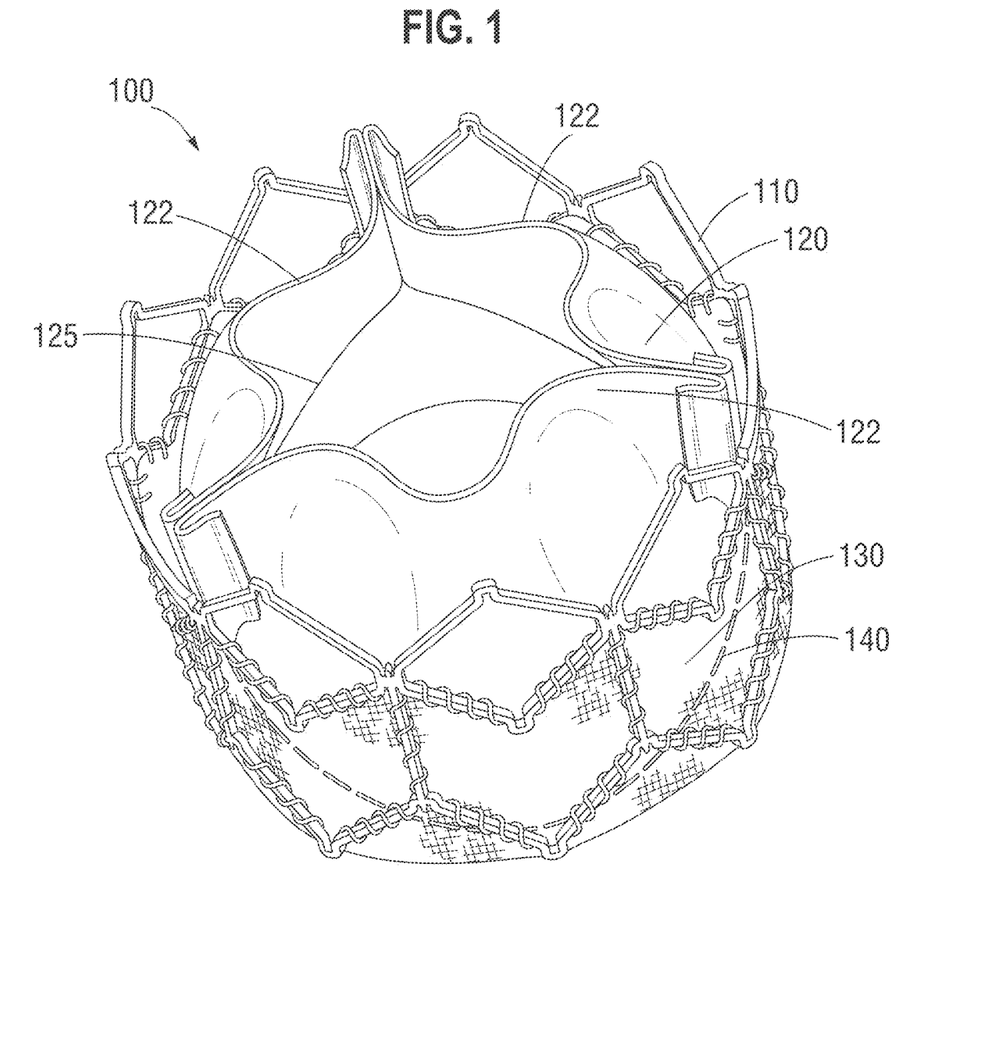
FIG. 1 is a top perspective view of a transcatheter heart valve in accordance with one embodiment of the present invention.

With reference now to FIG. 1 of the illustrative drawings, there is shown an embodiment of a transcatheter heart valve 100 that is adapted to be implanted in an aortic annulus, although it can be adapted to be implanted in other native annuluses of the heart. In one embodiment, the heart valve 100 can include a compressible frame 110, a valvular structure 120 comprising a plurality of leaflets 122, and a skirt 130. Exemplary transcatheter heart valves are described in U.S. Patent Application Publication No. 2012/0123529, published on May 17, 2012, the entire contents of which are incorporated by reference into this written description.

The frame 110 can comprise any suitable plastically-expandable materials (e.g., stainless steel, cobalt-chromium, etc.) or self-expanding materials (e.g., nitinol) as known in the art. The skirt 130 can be positioned on the frame 110 and can be made of any combination of suitable materials, such as a fabric, polyethylene terephthalate (PET), ultrahigh molecular weight polyethylene (UHMWPE), tissue, metal, sponge, or a polymer. In one embodiment, the skirt 130 can be secured to the inside of the frame 110 by sutures 140, which can comprise any suitable suture, such as polyester (for example, Ethibond PET suture, Ethicon), UHMWPE, polypropylene, and/or PTFE suture. In another embodiment, the sutures 140 track the curvature of a bottom edge, cusp region 125 of the leaflet structure 122.

As described in more detail below, in one embodiment, the heart valve 100, including the frame 110, valvular structure 120, skirt 130, and sutures 140, preferably does not comprise fluorinated materials.

Figure 2A:
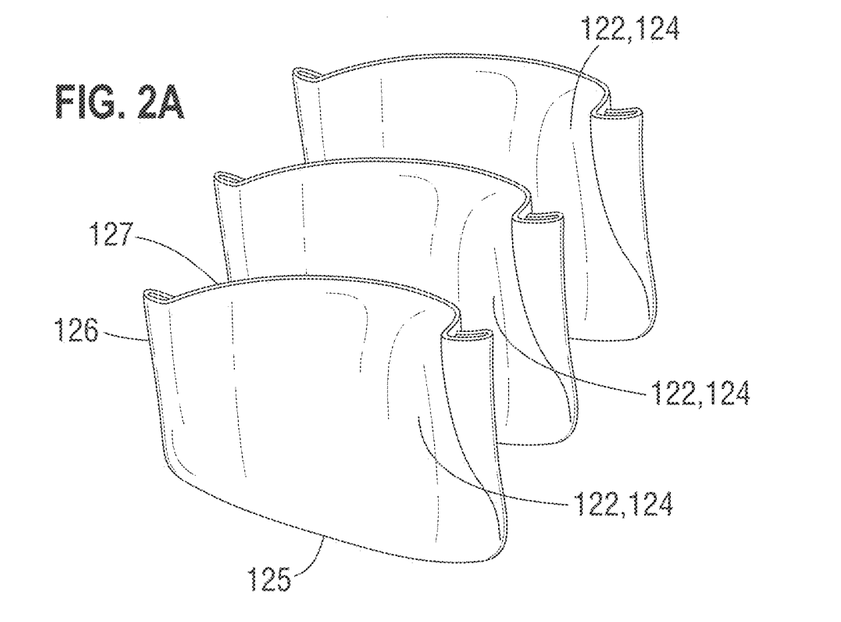
FIG. 2A is a perspective view of a plurality of leaflets in accordance with one embodiment of the present invention.
Figure 2B:
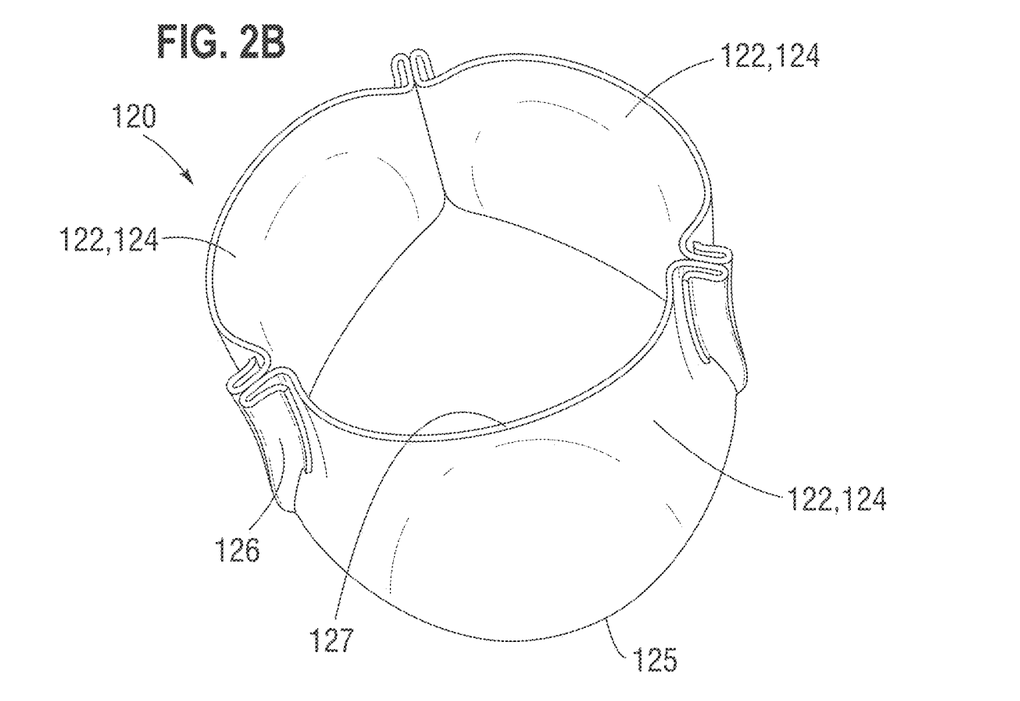
FIG. 2B is a perspective view of the plurality of leaflets joined together to form a leaflet assembly for a transcatheter heart valve, in accordance with one embodiment of the present invention.

With reference to FIGS. 2A and 2B, the leaflet structure 120 comprises a plurality of leaflets 122. In one embodiment, each of the plurality of leaflets 122 comprises a fixed, dry biological tissue, for example a fixed tissue that has been capped and dried with glycerol. An example of such tissue is referred to as "GLX tissue", which is described in U.S. Pat. No. 8,748,490, the entire contents which is incorporated by reference. Briefly, capping is believed to reduce calcification of the tissue by chemically modifying at least some of the functional groups that bind calcium or that are degradable to such a functional group, for example, amines, carboxylic acids, or carbonyl groups. In some embodiments, tissue, for example pericardium, is contacted with a capping agent, for example, ethanolamine, then contacted with a reducing agent, for example, sodium borohydride. Exemplary methods for drying tissue include contacting the tissue with glycerol, for example, with a glycerol/ethanol solution. Embodiments of each of the methods for sterilizing tissue disclosed herein are applicable to such tissue.

In one embodiment, each of the plurality of leaflets 122 comprises a decellularized, antigen-free, unfixed, dry biological tissue 124 that has been treated with a solution comprising a polyol or polyhydric alcohol.

The term "decellularized" means the tissue is substantially free of endogenous cells. Biological tissue includes a collagen skeleton (matrix) supporting cells therein. This extracellular structure supporting the cells is generally referred to as the "extracellular matrix" (ECM). In a "decellularized" tissue, the endogenous cells have been substantially removed from the ECM. For example, in one embodiment, at least about 70%, 80%, 90%, 95%, 99%, or more, of endogenous cellular material has been removed from the extracellular matrix. The presence of endogenous cellular material can be determined using any method known in the art.

The term "antigen-free" means the tissue is substantially free of endogenous antigen components (e.g., proteins, lipids, carbohydrates, nucleic acids). With respect to a decellularized tissue, the term refers to a decellularized tissue where the endogenous antigen components have been substantially removed. In one embodiment, at least about 70%, 80%, 90%, 95%, 99%, or more, of endogenous antigen components are removed from the decellularized tissue. In another embodiment, the antigen-free tissue does not elicit a significant immune response against the tissue. The presence of endogenous antigen components can be determined using any method known in the art. Exemplary methods of removing antigens from tissues and decellularized extracellular matrixes produced by such methods are described in U.S. Pat. No. 9,220,733, issued Dec. 29, 2015, the entire contents of which are incorporated by reference into this written description.

The term "unfixed" means the tissue has not been treated with a cross-linking fixative solution. Implanted biological tissue is often treated with a cross-linking solution to stabilize the tissue, as well as to reduce the antigenicity thereof. This process of stabilization is known as fixation. Generally, the biological tissue is fixed by cross-linking the amine groups of the proteins of the tissue with an aldehyde fixative solution (e.g., glutaraldehyde). Examples of chemical fixative agents that have been used to cross-link collagenous tissues include: formaldehyde, glutaraldehyde, dialdehyde starch, hexamethylene diisocyanate, and polyepoxy compounds.

Glutaraldehyde is one of the most widely used fixative agents for many commercially available bioprosthetic products, but it is known to contribute to calcification, which can result in undesirable stiffening or degradation of the heart valve. This damage to the collagenous tissue of the leaflets can lead to valve failure.

Glutaraldehyde solutions are also used as storage and terminal sterilizing solutions for devices that include tissue. The devices are stored and shipped in a jar containing such solutions, which are opened in the operating location. Because glutaraldehyde solutions are toxic to the healthcare workers and the patient, the device is rinsed thoroughly before implantation. Disposal of the glutaraldehyde solution may be regulated in some jurisdictions. The jar of solution also increases shipping weight, as well as limiting shipping flexibility because of the hazardous nature of the solution. Pre-attaching the device to an associated delivery device or system can also be impractical when the device is stored in glutaraldehyde solutions. Any or all of these limitations apply to any liquid storage media.

One strategy to avoid glutaraldehyde as a storage solution is to "dry" the biological tissue 124. Biological tissue comprises free water (between strands of the tissue) and bound water (within the strands of the tissue). The term "dry" refers to tissue that has bound water, but that is substantially devoid of free water. For example, in one embodiment, the plurality of leaflets comprising biological tissue are treated with a solution that causes the free water to be replaced with one or more other compounds (e.g., a polyol, glycerol, propylene glycol, a polyether, polyethylene glycol (PEG), polypropylene glycol, etc.). In another embodiment, the plurality of leaflets is treated with a solution comprising a polyol or polyhydric alcohol. In another embodiment, the polyol or polyhydric alcohol can comprise glycerol. The resulting "dry" tissue remains flexible, and can be stored outside of liquid for extended periods without degradation of functionality. This is contrasted with "dehydrated" tissue, which is substantially completely dry, for example, freeze-dried, such that substantially all of the water, free and bound, is removed.

In one embodiment, the biological tissue 124 can be pericardial tissue. In another embodiment, the biological tissue 124 can be pericardial tissue selected from the group consisting of porcine pericardial tissue and bovine pericardial tissue.

With continued reference to FIGS. 2A and 2B, in one embodiment, each of the plurality of leaflets 122 (comprising the biological tissue 124 described above) can include a cusp region 125, a commissure region 126, and a free edge region 127. In another embodiment, the plurality of leaflets 122 can be coupled to each other at the commissure regions 126 so that the free edge regions 127 are aligned.

Figure 3:
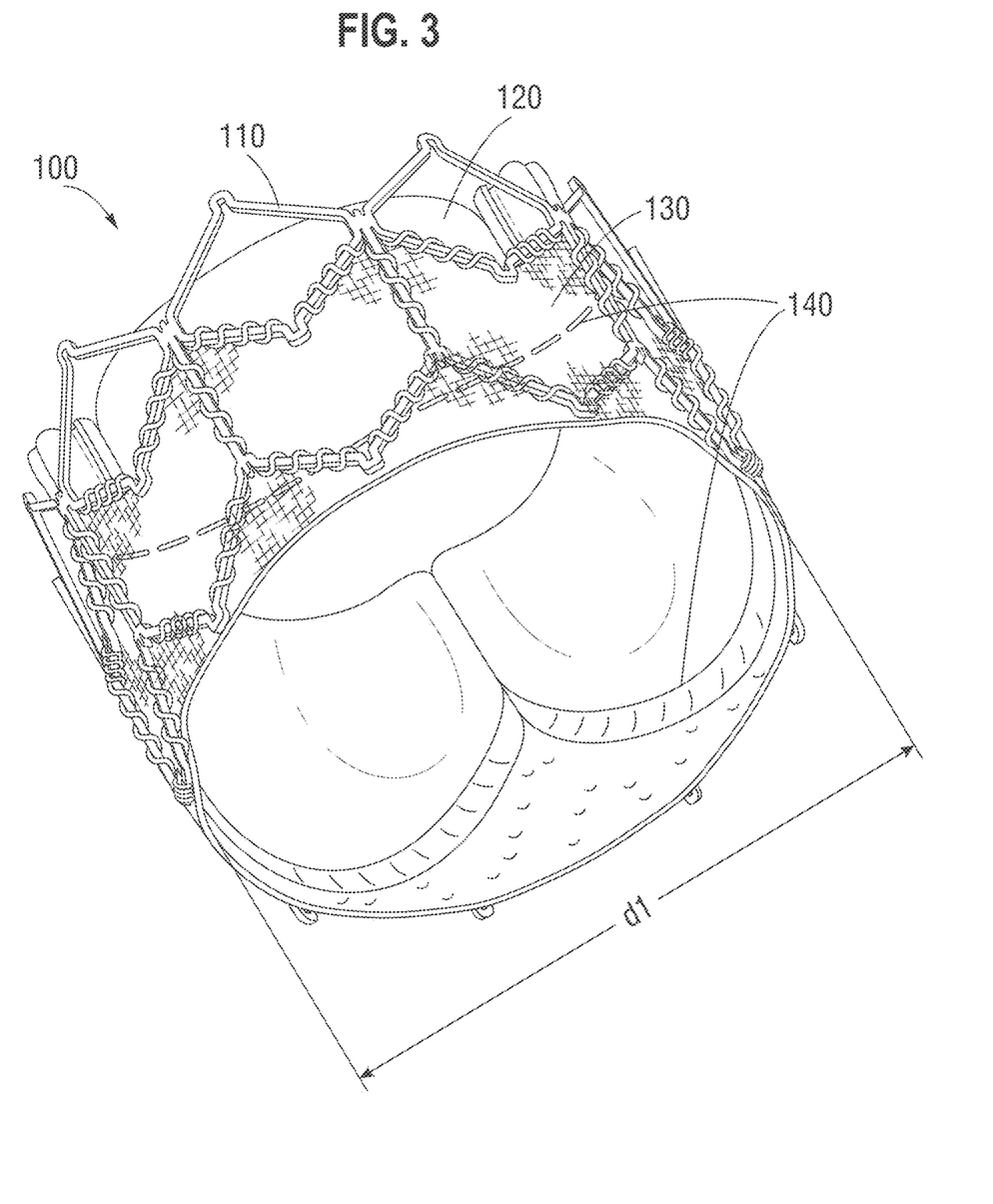
FIG. 3 is bottom perspective view of a transcatheter heart valve in an expanded configuration, in accordance with one embodiment of the present invention.

With reference to FIG. 3, in one embodiment, each of the plurality of leaflets 122 can be coupled to the compressible frame 110. In another embodiment, the plurality of leaflets 122 can be coupled to the compressible frame 110 in a configuration that allows the leaflet structure 120 to collapse in a tricuspid arrangement. In a further embodiment, a lower edge of the leaflet structure 120 can have an undulating, curved-scalloped shape (suture line 140 tracks the scalloped shape of the leaflet structure 120).

Figure 4:
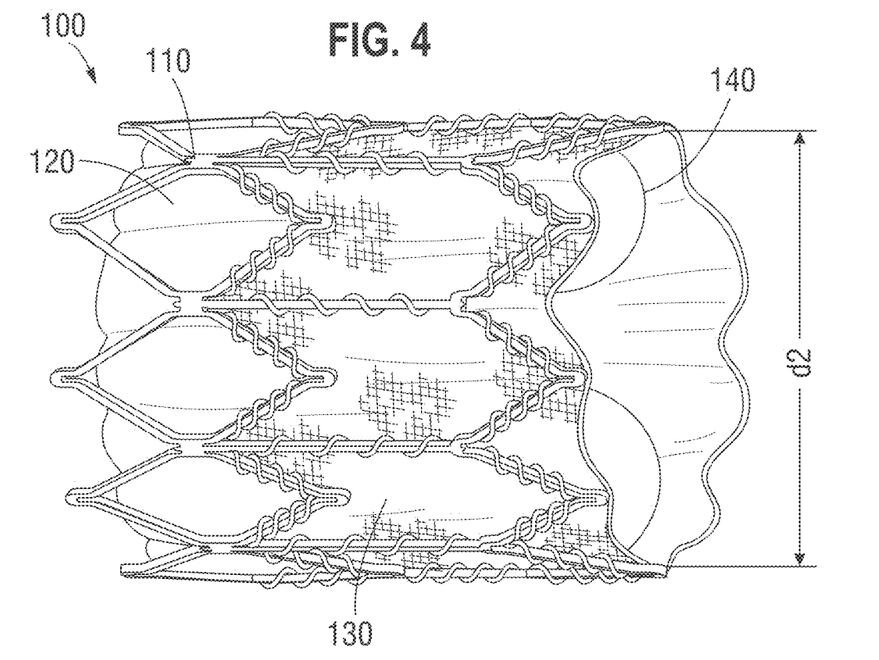
FIG. 4 is a side view of a transcatheter heart valve in a partially crimped configuration, in accordance with one embodiment of the present invention.
Figure 5:
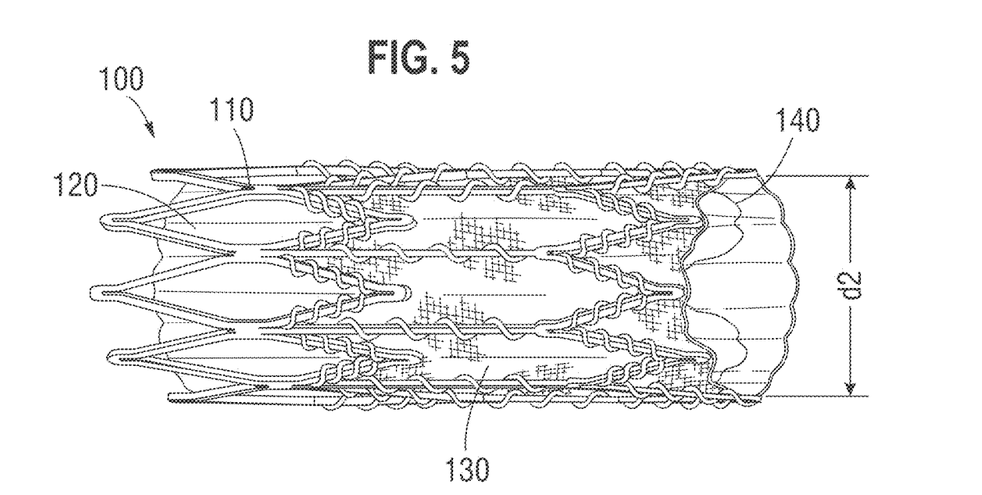
FIG. 5 is a side view of a transcatheter heart valve in a fully crimped configuration, in accordance with one embodiment of the present invention.

With reference to FIGS. 3-5, in one embodiment, the compressible frame 110 of the heart valve 100 can be compressed from an expanded configuration (FIG. 3) to a crimped configuration (e.g., FIGS. 4 and 5). In another embodiment, the frame 110 can be at least partially crimped in the crimped configuration. In a further embodiment, the frame 110 can be fully crimped in the crimped configuration.

The heart valve 100 can have a first diameter $d_1$ in the expanded configuration (FIG. 3) and a second diameter $d_2$ in the crimped configuration (e.g., FIGS. 4 and 5). As is shown in FIGS. 4 and 5, in one embodiment, the second diameter $d_2$ can be smaller than the first diameter $d_1$. In another embodiment, the second diameter $d_2$ can be less than about 50% of the first diameter $d_1$. In a further embodiment, the second diameter $d_2$ can be about 10% of the first diameter $d_1$.

Methods of crimping a compressible frame 110 are known in the art. For example, exemplary loaders for transcatheter heart valves and exemplary methods of crimping transcatheter heart valves are described in U.S. Patent Application Publication No. 2017/0049567, filed Aug. 16, 2016, the entire contents of which are incorporated by reference into this written description.

Figure 6A:
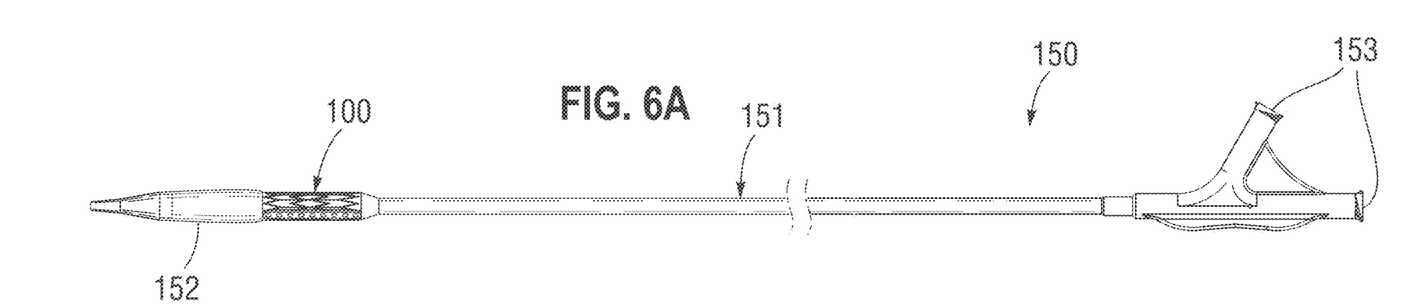
FIGS. 6A and 6B are broken side views of a transcatheter heart valve, in a crimped configuration, coupled to a delivery system, in accordance with one embodiment of the present invention.
Figure 6B:
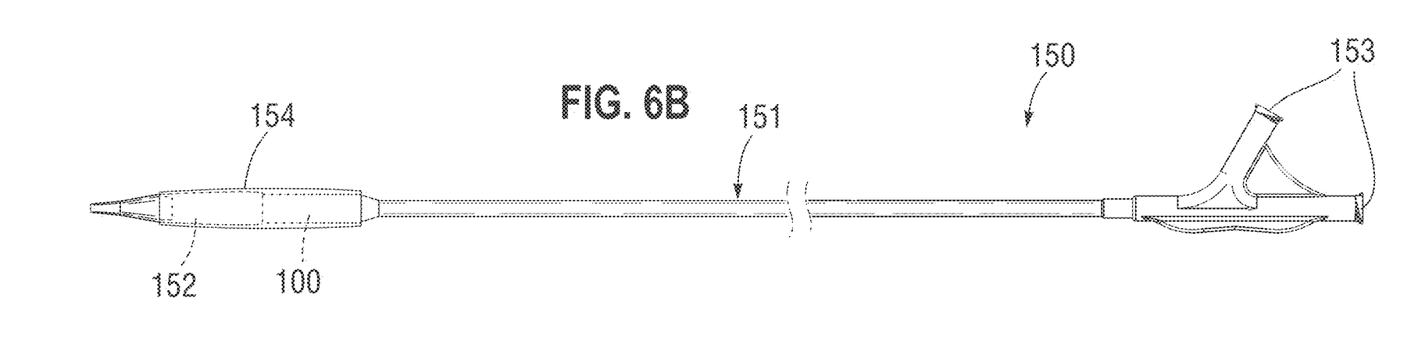

With reference to FIGS. 6A and 6B, in one embodiment, the heart valve 100 can be coupled to a delivery system 150. Expandable heart valves are known in the art, and the illustrated valve 100 is representative of a number of such valves that can be converted from a narrow, crimped configuration to a wider, expanded configuration. Typically, the valves are balloon expanded into position at a target annulus after having been advanced through the vasculature. The most common delivery routes commence at the femoral or carotid arteries, though other more direct routes through chest ports are also known. One particularly successful expandable prosthetic heart valve is the Edwards SAPIEN Transcatheter Heart Valve, available from Edwards Lifesciences of Irvine, California. The Edwards SAPIEN valve may be placed either through a transfemoral (RetroFlex 3 Transfemoral Delivery System from Edwards Lifesciences) or transapical (Ascendra Transapical Delivery System from Edwards Lifesciences) approach. FIG. 6A illustrates a system much like the RetroFlex 3 Transfemoral Delivery System from Edwards Lifesciences.

In one embodiment, the delivery system 150 can include an elongated catheter 151 having an expansion balloon 152 near a distal end of the catheter. The heart valve 100 can mount around the balloon 152 and be expanded by it. The system can further include proximal connectors 153, for example, Luer connectors, for delivery of balloon inflation fluid, passage of a guide wire, or other such functions. As described in more detail below, in another embodiment, the delivery system 150 preferably does not comprise fluorinated materials.

With particular reference to FIG. 6B, in a further embodiment, the heart valve 100 can be loaded within a sheath 154 associated with the delivery system 150. For example, the heart valve 100 can be compressed to a crimped configuration such that the second diameter $d_2$ is smaller than the inner diameter of the sheath 154. In this configuration, the loading step can be performed by causing the sheath 154 to move axially over the heart valve 100. In some embodiments, the heart valve 100 is at least partially self-expanding.

Figure 7A:
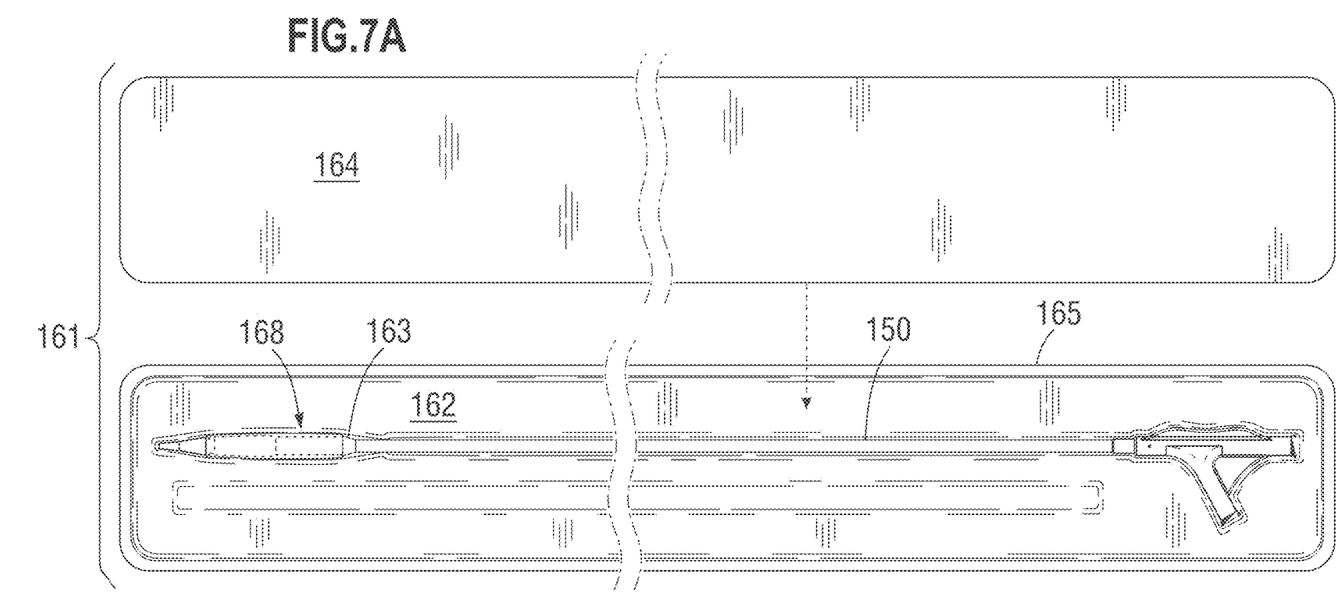
FIG. 7A is a broken plan view of a transcatheter heart valve, in a crimped configuration, coupled to a delivery system and partially packaged in a packaging system, in accordance with one embodiment of the present invention.
Figure 7B:
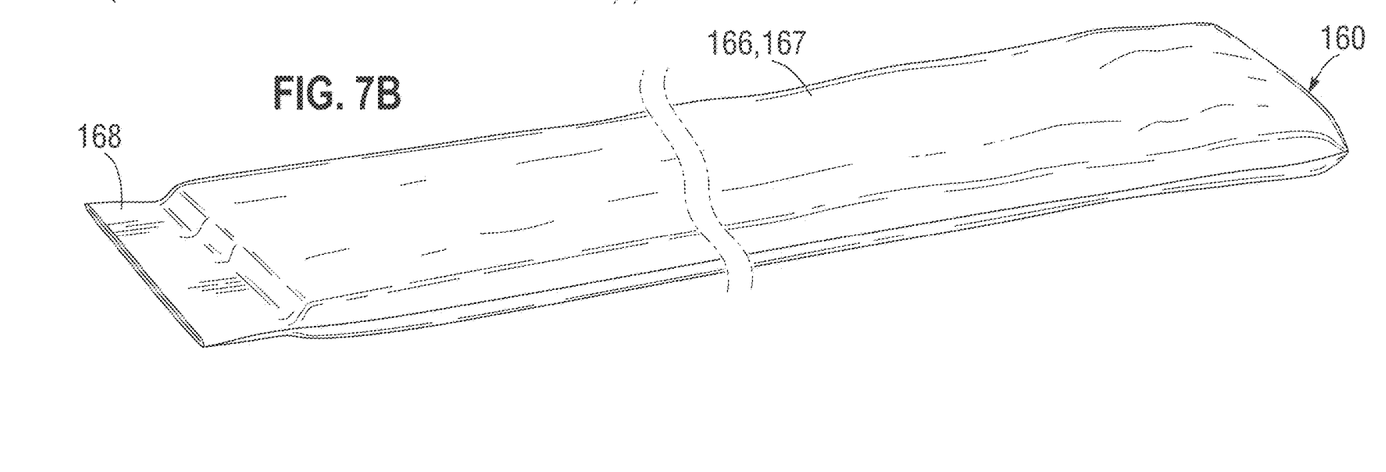
FIG. 7B is a broken perspective view of a of a fully packaged transcatheter heart valve in a packaging system, in accordance with one embodiment of the present invention.

With reference to FIGS. 7A and 7B, in one embodiment, the heart valve 100 can be packaged within a sealed packaging system 160 while the heart valve 100 is in the crimped configuration. In another embodiment, the packaging system 160 does not contain a liquid storage solution. In a further embodiment, the packaging system 160 can comprise a primary storage container 161 and a secondary storage container 167. As described in more detail below, in an additional embodiment, the packaging system 160 preferably does not comprise fluorinated materials.

For example, FIG. 7A illustrates a heart valve 100 and delivery system 150 packaged in an exemplary packaging system 160. In one embodiment, the packaging system 160 can comprise a primary storage container 161 and a secondary storage container 166. In another embodiment, the primary storage container 161 can include a primary storage container 161 in the form of a tray 162 and a sheet-like lid 164. In one embodiment, the tray 162 features a cavity 163, which retains and stabilizes the heart valve 100 within the primary storage container 161. The cavity 163 can be sized and configured to retain the heart valve 100 by itself, the heart valve 100 coupled to a delivery system 150, or the heart valve 100 loaded within a sheath 154 associated with the delivery system 150. In an additional embodiment, the lid 164 can adhere to an upper rim 165 of the tray 162.

FIG. 7B is a perspective view of a secondary storage container 166 in the form of a pouch 167. In one embodiment, the storage pouch 167 can receive the primary storage container 161. During packaging, the primary storage container 161 is placed within the pouch 167 and a seal 168 is closed to seal the packaging system 160. With the seal 168 closed, the sealed packaging system 160 provides a barrier against contamination from oxygen, moisture, or other contaminants.

Figure 8:
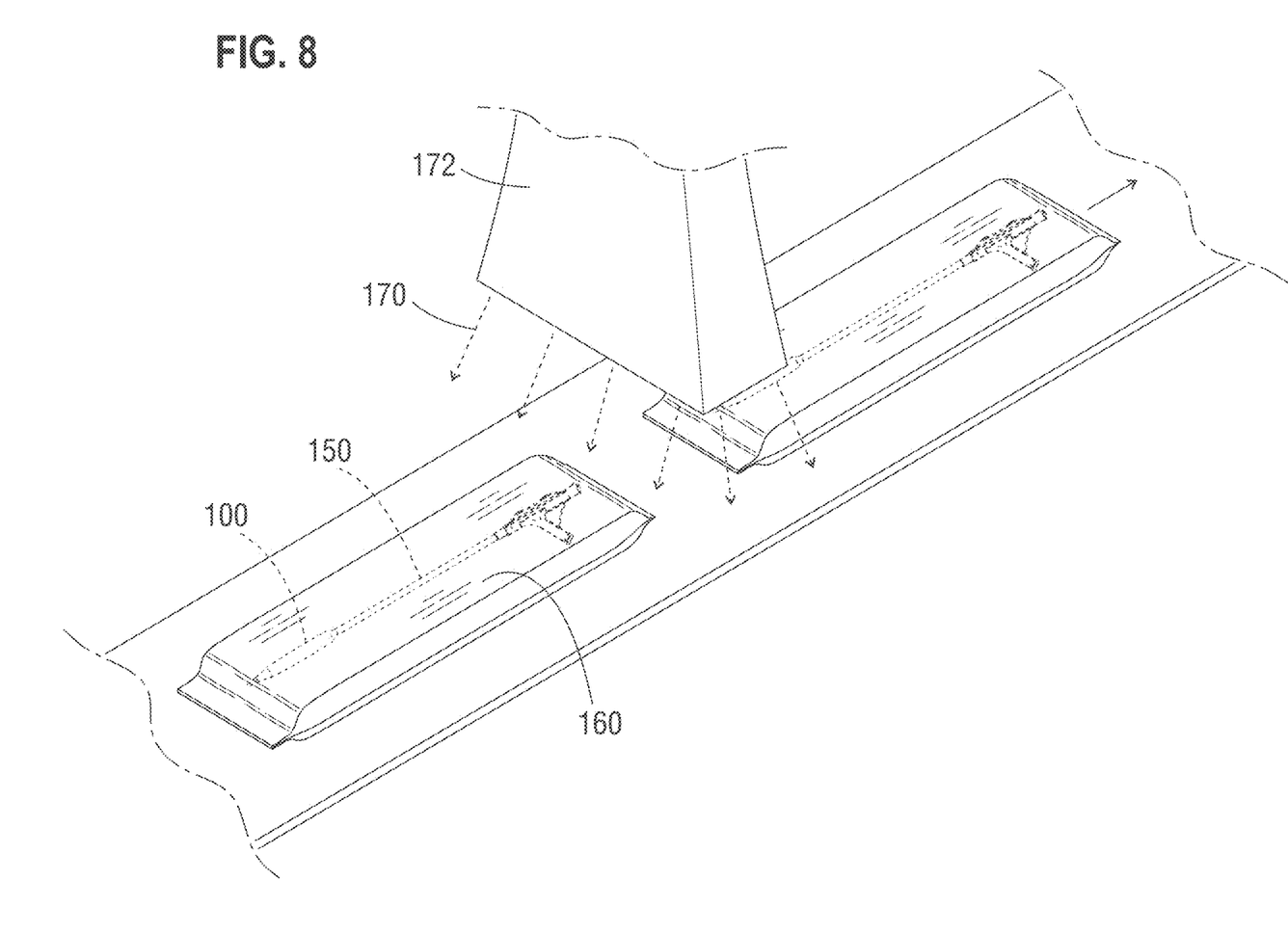
FIG. 8 is a perspective view of the packaging system of FIGS. 7A and 7B undergoing sterilization by electron beam radiation, in accordance with one embodiment of the present invention.

With reference to FIG. 8, in one embodiment, the heart valve 100 packaged within the sealed packaging system 160 can be sterilized with one or more cycles of electron beam (e-beam) radiation 170. For example, in one embodiment, the heart valve 100 in the sealed packaging system 160 can pass under a linear accelerator 172, which accelerates electrons from an electrical source. It is believed that the accelerated, high-energy electrons 170 interact with molecules in the sealed packaging system 160 and induce breaks in the DNA double helix of living organisms such as bacteria, which creates a sterile environment.

In some embodiments, one cycle of electron beam radiation consists of coverage on both the top side and bottom side of the packaging system 160. In one embodiment, each of the one or more cycles of electron beam radiation can comprise a dose of about 15-40 kGy. In another embodiment, each of the one or more cycles of electron beam radiation can comprise a dose of about 15-20 kGy. In a further embodiment, each of the one or more cycles of electron beam radiation can comprise a dose of about 15 kGy, about 16 kGy, about 17 kGy, about 18 kGy, about 19 kGy, or about 20 kGy.

In one embodiment, the heart valve 100 packaged within the sealed packaging system 160 can be sterilized with two or more cycles of electron beam radiation. In an additional embodiment, the heart valve 100 packaged within the sealed packaging system 160 can be sterilized with three cycles of electron beam radiation. In a further embodiment, the method can further comprise refrigerating the heart valve and the packaging system before the sterilizing step.

Electron beam sterilization of biological tissue is known in the art. For example, exemplary methods of sterilizing a biological tissue by exposing the tissue in saline solution to a beam of accelerated electrons are described in U.S. Pat. No. 6,203,755, filed Mar. 4, 1994, the entire contents of which are incorporated by reference into this written description.

Figure 9:
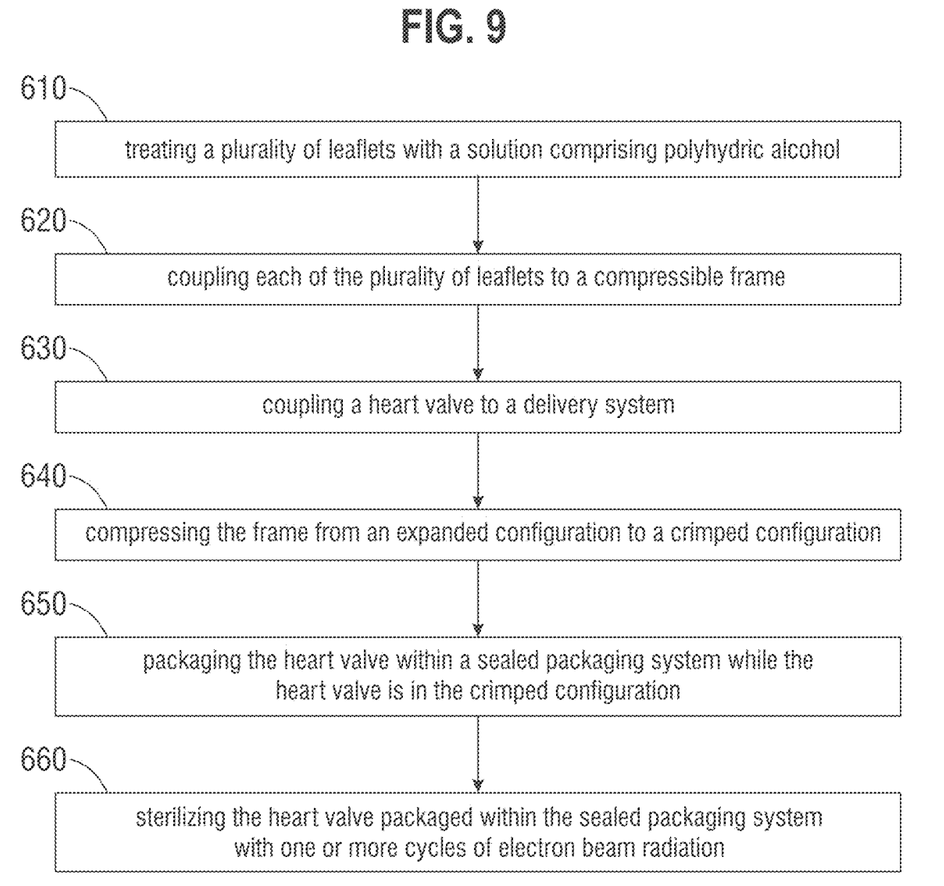
FIG. 9 illustrates a method of preparing a heart valve in accordance with one embodiment of the present invention.

With reference now to FIG. 9, some embodiments provide methods for preparing a sterilized heart valve. In one embodiment, the method comprises treating or contacting 610 a plurality of leaflets with a solution comprising a polyol or polyhydric alcohol. As described above, each of the plurality of leaflets comprises an unfixed, decellularized, antigen-free biological tissue. The treatment 610 with a solution comprising a polyol or polyhydric alcohol produces a "dry" biological tissue, as is understood in the art. In another embodiment, the method can further comprise forming a heart valve, wherein the forming step can comprise coupling 620 each of the plurality of leaflets to a compressible frame. In a further embodiment, the method can further comprise coupling 630 the heart valve to a delivery system. In an additional embodiment, the method can further comprise compressing 640 the frame from an expanded configuration to a crimped configuration. In yet another embodiment, the method can further comprise packaging 650 the heart valve within a sealed packaging system while the heart valve is in the crimped configuration. In one embodiment, the method can further comprise sterilizing 660 the heart valve packaged within the sealed packaging system with one or more cycles of electron beam radiation.

It should be understood that each feature, concept, or step is independent, and can be combined with any other feature, concept, or step disclosed in this application. Moreover, certain steps can be omitted entirely, as will be understood by a person of ordinary skill in the art.

For example, another embodiment comprises compressing 640 a compressible frame of a heart valve from an expanded configuration to a crimped configuration, packaging 650 the heart valve within a sealed packaging system while the heart valve is in the crimped configuration, and sterilizing 660 the heart valve packaged within the sealed packaging system with one or more cycles of electron beam radiation. In this embodiment, the heart valve can comprise the frame and a plurality of leaflets coupled to the frame. In one embodiment, each of the plurality of leaflets can comprise an unfixed, decellularized, antigen-free biological tissue that has been treated with a solution comprising a polyol or polyhydric alcohol. In an alternative embodiment, each of the plurality of leaflets can comprise a dry, unfixed, decellularized, antigen-free biological tissue.

Dry heart valves are commonly sterilized with ethylene oxide (EO, ETO). However, EO sterilization does not work well on heart valves in a compressed configuration. When the heart valve is pre-crimped, the EO gas is unable to penetrate and effectively sterilize the surfaces of the heart valve. One method for working around this limitation is contacting the uncrimped device with EO, following by contacting the partially crimped device with EQ. Each round of EO potentially damages the tissue and/or changes the leaflet shape.

Leaflet structures 120 comprising the biological tissues 124 described above are able to undergo a more efficient electron beam sterilization process while in a compressed configuration.

It should be appreciated from the foregoing description that the present invention provides a method of preparing a transcatheter heart valve that can be crimped, packaged, and sterilized at the manufacturer's site. The heart valve processed according to these methods minimizes crimping error and, as suggested by the examples below, exhibits advantageous mechanical properties as well as favorable biological and histological responses.

Other objectives, features, and advantages of the present embodiments will become apparent from the following specific examples. The specific examples, while indicating specific embodiments, are provided by way of illustration only. Accordingly, the present invention also includes those various changes and modifications within the spirit and scope of the invention that may become apparent to those skilled in the art from this detailed description. The following examples are illustrative only, and are not limiting of the disclosure in any way whatsoever.

Example 1

One study compared the effect of sterilization methods on crimped tissue. In the study, valves were constructed from GLX tissue leaflets as described in U.S. Pat. No. 8,748,490 mounted in Edwards Sapien 3 valve-frames. The resulting devices were crimped onto expansion balloons and sterilized either with ethylene oxide (EO or electron-beam. The heart valves sterilized with the EO process were subjected to a dosage from about 436 to about 558 mg/L of gas over 6 hours and a temperature of from about 48° C. to about 54° C. The heart valves sterilized with the e-beam process were subjected to a maximum dose of about 30 kilogray (kGy). A control valve was sterilized by the e-beam process in an expanded configuration.

The valves were then aged and expanded to the labeled size. After eight weeks, the crimped tissue sterilized by the EO process exhibited a deformed leaflet structure, with a triangular opening and a yellow discoloration. It is believed that cross-linking, and possibly heat generated in the EO process caused the leaflets to shape-set and to deform in the crimped configuration.

The tissue in the valves that were pre-crimped and sterilized with e-beam was more flexible and did not exhibit the same level of shape deformity or discoloration. The shape, color, and pliability of these valves was much closer to that of the control valve, which was e-beam sterilized in the expanded configuration.

In hydrodynamic testing, all of the valves exhibited good coaptation with either no or a very small central hole. All valves exhibited some mismatch and puckering.

Each of the leaflets was then removed from each of the heart valves, and three dimensions of each leaflet measured: a width at the top or free edge; a width at a mid-height; and a height. The dimensions of the EO and e-beam sterilized crimped leaflets were similar.

Example 2

One study analyzed the effect of e-beam sterilization on the tensile strengths of materials commonly used in heart valves. In the study, cloth materials (i.e., knitted polyester, PET woven 70 mm, and PET woven ribbon 65 HD) and suture materials (i.e., PET (Ethibond 4-0 suture, Ethicon), UHMWPE (Force Fiber suture, Teleflex Medical), PTFE, and PTFE round) underwent e-beam sterilization at a maximum dose of about 30 kilogray. The tensile strength of each of the various materials was tested against the tensile strength of the respective control that underwent EO sterilization under the conditions described in Example 1.

Figure 10:
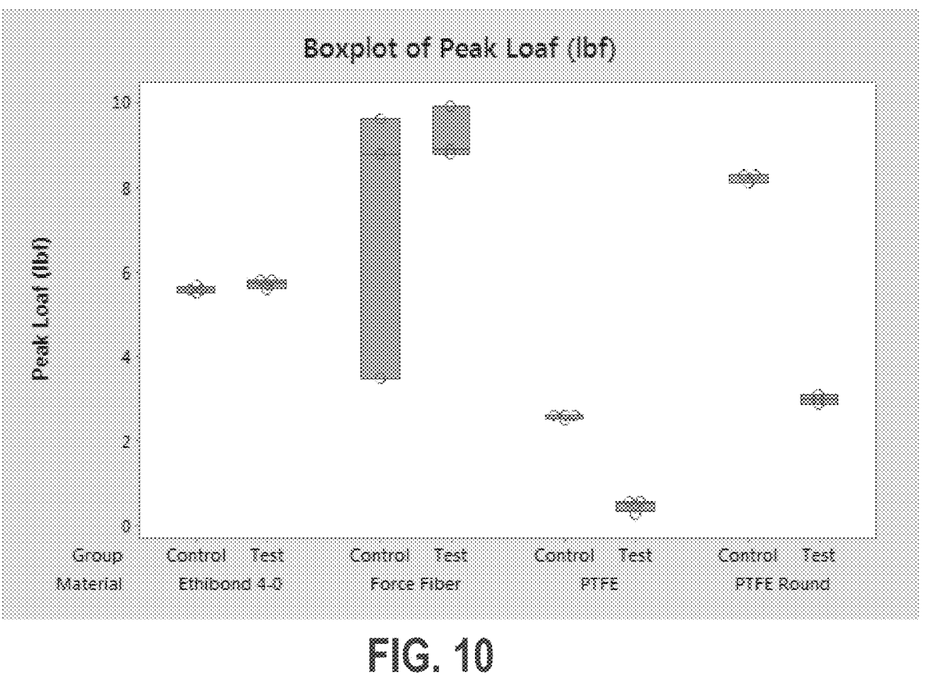
FIG. 10 is a graph illustrating the effects of different sterilization protocols on the tensile strengths of selected sutures.

With reference to FIG. 10, e-beam sterilization degraded PTFE suture tensile strength by at least 50%, while the tensile strengths of the non-fluorinated sutures materials were unaffected. Similarly, e-beam exposure did not degrade the tensile strengths of the fabrics.

Current valves often include components, such as suture, that comprise PTFE. It is believed that contacting these materials with an electron beam cleaves the fluorinated polymers, which changes the material properties of the plastic, causing embrittlement. This problem is not present with non-fluorinated materials under the experimental conditions, such as ultra-high molecular weight polyethylene materials.

Example 3

The effect of e-beam sterilization on tissue calcification was studied in rabbits using the experimental conditions of Example 3 of U.S. Pat. No. 8,748,490, the disclosure of which is incorporated by reference. In this study, dry, fixed bovine pericardium (GLX) and dry, unfixed, decellularized, antigen-free bovine pericardium ("unfixed") were sterilized by e-beam or by EO as described in Example 1. Control samples were bovine pericardium fixed with glutaraldehyde and stored in a glutaraldehyde terminal sterilization solution.

Histological analysis of the sterilized unfixed tissue showed that the e-beam-sterilized pericardium retained a collagen "crimp" structure, but that the EO sterilization eliminated this structure. EO-sterilized unfixed tissue was not dimensionally stable, instead curling and crimping on itself, behavior which was not observed in the e-beam sterilized unfixed tissue. No microstructural differences were observed between the e-beam- and EO-sterilized GLX pericardium.

The samples were implanted in rabbits and the calcification levels were measured in the explanted tissue. In general, the more calcified a tissue becomes, the less durable it is. With reference to Table 1, which tabulates the mean calcium in μg per mg of dry tissue, electron beam sterilization did not increase the calcification in the GLX or in the unfixed tissue.

TABLE 1

|  | N | Calcium (μg/mg) |
| --- | --- | --- |
| Control | 22 | 170.41 |
| GLX, EO | 22 | 101.5 |
| GLX, e-beam | 22 | 103.3 |
| Unfixed, EO | 20 | 6.81 |
| Unfixed, e-beam | 22 | 3.1 |

Explanted EO-sterilized pericardium exhibited significantly greater degradation compared with the e-beam sterilized samples.

It should be appreciated from the foregoing description that the present disclosure provides a method of preparing a transcatheter heart valve that can be crimped, packaged, and sterilized at the manufacturer's site. A heart valve processed according to these methods minimizes crimping error and exhibits advantageous mechanical properties as well as favorable biological and histological responses.

Specific methods, devices, and materials are described, although any methods, devices, and materials similar or equivalent to those described can be used in the practice or testing of the present embodiment. Unless defined otherwise, all technical and scientific terms used in this written description have the same meanings as commonly understood by one of ordinary skill in the art to which this embodiment belongs.

The terms "a," "an," and "at least one" encompass one or more of the specified element. That is, if two of a particular element are present, one of these elements is also present and thus "an" element is present. The terms "a plurality of" and "plural" mean two or more of the specified element.

The term "or" used between the last two of a list of elements means any one or more of the listed elements. For example, the phrase "A, B, or C" means "A, B, and/or C," which means "A," "B," "C," "A and B," "A and C," "B and C," or "A, B, and C."

The term "coupled" generally means physically coupled or linked and does not exclude the presence of intermediate elements between the coupled items absent specific contrary language.

Without further elaboration, it is believed that one skilled in the art, using the proceeding description, can make and use the same to the fullest extent. Persons skilled in the art will appreciate that various modifications of the embodiments described herein can be made without departing from the teachings of this disclosure, the scope of which is defined only by the following claims.

What is claimed is:

1. A method of sterilizing a prosthetic heart valve, the method comprising:
   radially compressing a compressible frame of a heart valve from an expanded configuration to an at least partially crimped configuration, the heart valve comprising the frame and a plurality of leaflets coupled to the frame, wherein each of the plurality of leaflets comprises a dry, unfixed, decellularized pericardial tissue, wherein the tissue has not been treated with a cross-linking fixative solution;
   packaging the compressed heart valve within a sealed packaging system; and
   sterilizing the compressed heart valve packaged within the sealed packaging system with one or more cycles of electron beam radiation.

2. The method of claim 1, wherein each of the one or more cycles of electron beam radiation comprises a dose of about 15-40 kGy.

3. The method of claim 1, further comprising treating the plurality of leaflets with a solution comprising a polyol or polyhydric alcohol.

4. The method of claim 3, wherein the polyol or polyhydric alcohol is glycerol.

5. The method of claim 1, further comprising coupling the heart valve to a delivery system.

6. A method of preparing a sterilized heart valve, comprising:
   coupling a heart valve to a delivery system, the heart valve comprising a compressible frame and a plurality of leaflets coupled to the frame, wherein each of the plurality of leaflets comprises a dry, unfixed, decellularized, antigen-free pericardial tissue, wherein the tissue has not been treated with a cross-linking fixative solution;
   compressing the frame of the heart valve from an expanded configuration to a crimped configuration;
   packaging the compressed heart valve within a sealed packaging system while the frame of the heart valve is in the crimped configuration; and
   sterilizing the compressed heart valve packaged within the sealed packaging system with one or more cycles of electron beam radiation, wherein each of the one or more cycles of electron beam radiation comprises a dose of about 15-40 kGy.

7. The method of claim 6, wherein the pericardial tissue is selected from the group consisting of porcine pericardial tissue and bovine pericardial tissue.

8. The method of claim 6, further comprising loading the heart valve within a sheath associated with the delivery system.

9. The method of claim 8, wherein the loading is performed by causing the sheath to move axially over the heart valve.

10. The method of claim 6, wherein the frame is at least partially crimped in the crimped configuration.

11. The method of claim 6, wherein the frame is fully crimped in the crimped configuration.

12. The method of claim 6, wherein the heart valve has a first diameter when the frame is in the expanded configuration and a second diameter when the frame is in the crimped configuration, wherein the second diameter is smaller than the first diameter.

13. The method of claim 12, wherein the second diameter is less than about 50% of the first diameter.

14. The method of claim 13, wherein the second diameter is about 10% of the first diameter.

15. The method of claim 6, wherein each of the one or more cycles of radiation comprises a dose of about 15-20 kGy.

16. The method of claim 6, wherein the heart valve packaged within the sealed packaging system is sterilized with two or more cycles of electron beam radiation.

17. The method of claim 6, wherein the heart valve packaged within the sealed packaging system is sterilized with three cycles of electron beam radiation.

18. The method of claim 6, further comprising refrigerating the heart valve and the packaging system before the sterilizing step.

19. The method of claim 6, wherein the heart valve does not comprise fluorinated materials.

20. The method of claim 6, wherein the packaging system does not contain a liquid storage solution.

* * * * *